(12) United States Patent
Meyer et al.

(10) Patent No.: US 6,177,550 B1
(45) Date of Patent: Jan. 23, 2001

(54) PROCESS FOR EXTRACTION OF A GROWTH FACTOR COMPLEX

(75) Inventors: Hans Meyer; Hermann Wasmer, both of Riehen; Dieter Hofmann, Reinach, all of (CH)

(73) Assignee: IPR Institute for Pharmaceutical Research AG, Riehen (CH)

( * ) Notice: Under 35 U.S.C. 154(b), the term of this patent shall be extended for 0 days.

(21) Appl. No.: 09/153,194

(22) Filed: Sep. 15, 1998

Related U.S. Application Data

(63) Continuation of application No. PCT/CH97/00097, filed on Mar. 11, 1997.

(30) Foreign Application Priority Data

Mar. 15, 1996 (CH) .......................................... 00686
Jul. 13, 1996 (EP) ................................. 96111328

(51) Int. Cl.[7] .................................................. C07K 3/02
(52) U.S. Cl. .......................... 530/412; 530/399; 530/418; 530/419; 424/198.1
(58) Field of Search ..................................... 530/399, 412, 530/418, 419; 424/198.1

(56) References Cited

U.S. PATENT DOCUMENTS 4,528,186 * 7/1985 Nishimura et al. .................... 424/99

\* cited by examiner

*Primary Examiner*—Michael P. Woodward
*Assistant Examiner*—Anish Gupta
(74) *Attorney, Agent, or Firm*—Pennie & Edmonds LLP

(57) ABSTRACT

The process of the invention for the extraction of a Growth Factor Complex is characterized in that water is added to natural and growth factors containing material, the pH value is adjusted to 2.5 to 3.2 by the addition of acid, the resulting precipitate is separated from the supernatant, the Growth Factor Complex in the aqueous solution is precipitated by the addition of an organic solvent miscible with water, separated from the liquid phase and dried, and the powder obtained is, if desired, dialyzed.

6 Claims, 2 Drawing Sheets

PROCESS FOR EXTRACTION OF A GROWTH FACTOR COMPLEX

Figure 1:
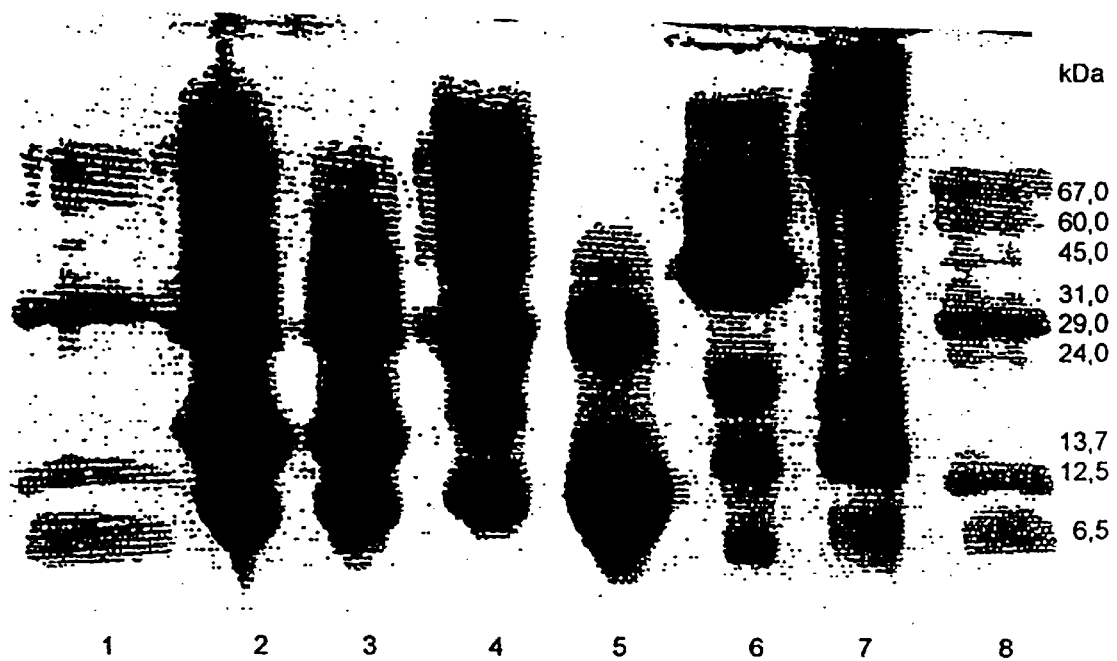

This is a continuation, of PCT application no. PCT/CH97/00097 filed Mar. 11, 1997.

BRIEF SUMMARY OF THE INVENTION

The process of the invention for the extraction of a Growth Factor Complex is characterized in that water is added to natural and growth factors containing material, the pH value is adjusted to 2.5 to 3.2 by the addition of acid, the resulting precipitate is separated from the supernatant, the Growth Factor Complex in the aqueous solution is precipitated by the addition of an organic solvent miscible with water, separated from the liquid phase and dried and the powder obtained is, if desired, dialyzed.

BACKGROUND OF THE INVENTION

Growth factors are polypeptides of particular interest since they possess specific biological properties. Because of their special properties, the growth factors per se and in particular in combination are promising compounds of medicaments and cosmetics. Until now, the extraction of growth factors was a very time- and cost-consuming process which yielded predominantly single growth factors.

According to patent specification EP 313 515, a process for the isolation of the Milk Growth Factor (MGF) is described, where the starting material is subject to one or more chromatographic techniques and, if required, to further purification steps. With this extensive extraction process, a single growth factor is obtained from milk. WO 95/29933 describes the manufacture of several growth factors from milk. For this laborious process, pasteurized whey which has been submitted to micro-filtration is used as starting material (details are described in Australian patent specification No. 645589). The protein containing material is then applied to a cation exchange resin, equilibrated with 50 mM sodium citrate buffer pH 6.5. After a wash procedure with the same buffer, the protein is eluted with 0.4 M NaCl, diafiltrated against water, concentrated by means of ultrafiltration and lyophilized. Further purification steps yield fractions which contain 10 mg lactalbumin per ml (the fractions each consist of 100 $\mu$l). The patent specification WO 95/26984 describes the manufacture of an insulin-like growth factor from cows milk by cation exchange chromatography and subsequent dialysis. JP 6279312 also describes the manufacture of an insulin-like growth factor by heating of milk or whey to a specific temperature, centrifuging and passing the supernatant through an 8 kDa ultrafilter.

In contrast to the prior art the present invention discloses a simplified and cheap process with a high yield: From 1 kg commercial milk powder, 350 g to 420 g of carbohydrates, in which the active Growth Factor Complex is contained, are isolated. This complex consists—as already mentioned hereinabove to the greater part of lactose. Using cow's milk as starting material, the protein proportion is about 5%. If desired, most of the lactose may be removed by dialysis. For therapeutic purposes, however, undialyzed lactose-containing material is advantageous since a correct and reproducible dosage of the biologically highly active factors can in this manner be managed considerably simpler.

The action of individual milk growth factors has been investigated in detail during the last 15 years. It has been shown inter alia that the biologically active polypeptides have physiological functions such as regulation, stimulation or inhibition of various cell functions (Am. J. Med. Sci., 1991, 301, 2, 124–132). Pittelkow M. R. (Advances in Dermatology, 1991, 7, 55–81) could demonstrate that some milk peptides act as natural mediators of cellular processes which are important for the maintenance of the dermis structure.

The biological activity of growth factors may be determined with the aid of the migration test and/or proliferation test. The migration test is performed according to Bürk R. R. (Proc. Nat. Acad. Sci., 1973, 70, 2, 369–372): After cells (e.g. Balb/C-3T3-fibroblasts) have grown to a confluent monolayer, a 10 mm wide area is removed with a razor blade. By addition of milk growth factors the cell migration is increased as compared to the control. The proliferation test, also carried out on the Balb/C-3T3-fibroblasts revealed an increased cell growth upon treatment of fibroblasts with milk growth factors.

In the prior art, the use of single factors or a combination of two growth factors have been described. WO 95/29933 describes a growth factor abbreviated as GFE-2 that is produced from milk. This growth factor is used for wound treatment as well as for gastrointestinal disturbances, illnesses or ulcers. EP 367 447 describes the use of the Human Cell Transforming Growth Factor for growth stimulation of epithelial cells e.g. for treatment of wounds, ulcers, burns or for reepithelization after radiotherapy. FR 2472385 and FR 2533438 describe the cosmetic use of various isolated growth factors. JP 6040858 uses the Fibroblast Growth Factor in a hair tonic for prevention and treatment of alopecia. EP 313 515 describes the use of a milk growth factor in tooth paste, mouthwashes, cosmetic and nutritional preparations.

The present invention contains a natural set of growth factors that may act in concert. As disclosed in EP 313 515, various growth factors act synergistically when combined. In the patent specification mentioned, a milk growth factor is combined with the Epidermal Growth Factor (EGF) or the Transforming Growth Factor $\alpha$ (TGF-$\alpha$) in order to achieve a better wound healing. The present invention has the advantage that the end product already contains of a combination of various growth factors.

DETAILED DESCRIPTION OF THE INVENTION

Natural and growth factors containing materials (in the following termed "starting materials") may be the following: milk from mammals such as human milk, cow's milk, goat's milk, sheep's milk, mare's milk asf. and the corresponding wheys, bird's eggs such as hen's eggs, duck's eggs, ostrich's eggs asf., fish roe such as trout roe, sturgeon roe asf., blood from mammals such as human blood, beef blood, goat blood, sheep blood, horse blood asf., urine from mammals such as human urine, cattle urine, goat urine, sheep urine, horse urine asf., as well as bee's honey and plant seeds.

Preferred starting materials are human milk, cow's milk, hen's eggs, trout roe and beef blood. A particularly preferred starting material is skimmed cows milk or its whey obtained from cheese-making or a commercially available dried whey, which is obtained e.g. by spray drying. The process of the invention for the extraction of the Growth Factor Complex may be used on all examples stated herein as starting materials, and generally on all starting materials that contribute to growth or grow themselves (e.g. seeds). In general terms, the process of the invention may be used on any peptide- or protein-containing starting material.

To solid starting materials, water is added to bring them to a homogeneous solution before further treatment. Fat containing starting materials are defatted before treatment in a conventional manner, e.g. by skimming.

The extraction of the Growth Factor Complex according to the invention is described hereinafter; as an example that of the Growth Factor Complex from skimmed milk, where the solid dry substance is more concentrated than in unprocessed milk. Such starting materials with a high content of solid milk dry substance are manufactured in that natural milk is, after skimming, concentrated by evaporation of water under mild conditions or in that dried milk obtained from skimmed milk is mixed with a suitable amount of water. Skimmed milk containing at least 100 g/l of dry substance and especially dried milk from skimmed cow's milk are the preferred starting materials.

To adjust of the pH value of the solution containing the starting material to 2.5 to 3.2, generally non-oxidizing mineral acids and organic acids such as mono-, di- and tricarboxylic acids as well as hydroxy acids derived therefrom may be used. Suitable mineral acids are hydrochloric acid, sulphuric acid and phosphoric acid. Suitable organic acids are formic acid, acetic acid, propionic acid, butyric acid, oxalic acid, malonic acid, succinic acid, glycolic acid, lactic acid (α-hydroxypropionic acid), β-hydroxypropionic acid, malic acid, tartaric acid, ascorbic acid and citric acid. The acids are best used as acqueous solutions. Preferred acids are formic acid, acetic acid, lactic acid and citric acid. Particularly preferred is 80% lactic acid. The amount of acid required for adjusting the pH value is preferably added to the milk as an aqueous acid solution with vigorous stirring at room temperature the addition generally proceeds without exothermic reaction. Preferably, the pH value is adjusted to 2.5 to 2.7 by acid addition. After that the mixture is preferably stirred for further 15 to 30 min.

The precipitate that results from acid addition may be separated off by filtration, e.g. through a close-meshed wire gauze or through a straining cloth or by centrifugation. It is preferable to free the precipitate from the adhering growth factors containing aqueous solution by pressing. A finely structured, sticky precipitate is obtained. It is furthermore preferable to filter the aqueous solution once again, e.g. through a liquor filter or a pleated filter, in order to completely separate the precipitate obtained by acid treatment from the supernatant. The growth factors containing aqueous solution which is obtained by separation of the precipitate with acid is an important intermediate product and also subject of the present invention.

Possible organic solvents miscible with water that are added to the aqueous solution obtained after separating off the precipitates may be: lower alkanols such as as methanol, ethanol, n-propanol or isopropanol, as well as lower ketones such as acetone, methylethyl ketone and diethyl ketone. Preferred organic solvents miscible with water are isopropanol and acetone. Particularly preferred is acetone.

Before addition of an organic solvent miscible with water for separating off the Growth Factor Complex, the growth factors containing aqueous sulotion is cooled to a temperature of 0° C. to 10° C., preferably to 3° C. to 5° C. To precipitate the Growth Factor Complex, an organic solvent miscible with water is generally added to the aqueous solution with stirring and the organic solvent and the aqueous solution are used at a volume ratio of 2:1 to 10:1. The volume ratio of the organic solvent miscible with water to the aqueous solution is preferably 4:1 to 6:1. The precipitated Growth Factor Complex may be separated off by filtration or by centrifugation. It is preferably washed with the solvent used for separation and dried at room temperature or under vacuum at slightly increased temperatures.

Subsequently, the resulting powder may, if desired, be dialyzed against running ion free water for further concentration, the permeability of the diaphragm being selected so that only molecules with a molecular weight of less than 3.5 kDa are passed through.

It has been found that the biological activity of the product obtained increases if it is extracted with a fat soluble solvent after drying. The extraction may be carried out continuously or discontinuously in a manner known per se with usual equipment. The continuous extraction may e.g. be performed with a Soxhlet apparatus. The discontinuous extraction is preferably carried out by suspending the product obtained by the process of the invention in the solvent after drying. The suspension is stirred for some minutes, e.g. 5 to 20 min, and the product is separated off and dried. Possible fat soluble solvents are preferably low boiling halogenated aliphatic hydrocarbons, such as methylene chloride, chloroform and carbon tetrachloride. A preferred solvent is methylene chloride.

The Growth Factor Complex produced according to the process of the invention from cow's milk is a white crystalline powder. The active polypeptides contained in this powder, the so called growth factors, are known from literature (M. R. Pittelkow, Advances in Dermatology, 1991, 7, 55). The best known and best investigated milk growth factors are Transforming Growth Factor α (TGF-α), Transforming Growth Factor β (TGF-β), Fibroblast Growth Factor (FGF), Platelet Derived Growth Factor (PDGF), Insulin-like Growth Factor (IGF) and Epidermal Growth Factor (EGF).

Figure 2:
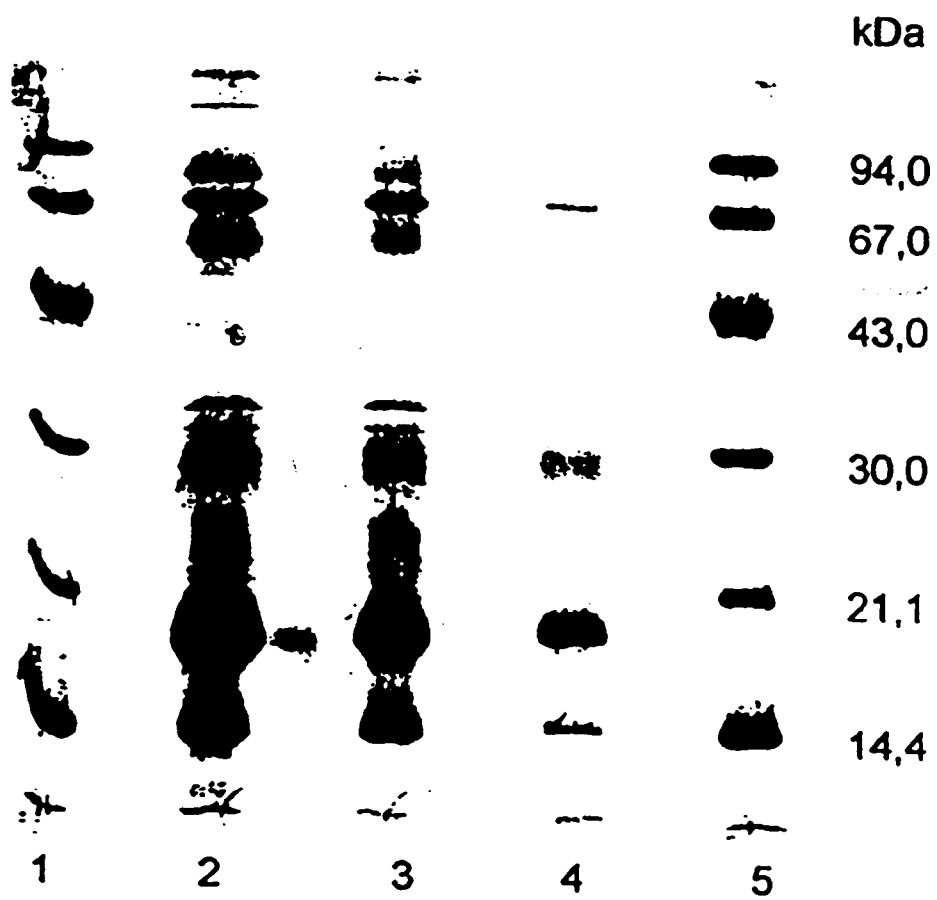

All previously described starting materials may be used for the process of the invention for extraction of a Growth Factor Complex. However, the resulting Growth Factor Complexes differ in the composition of active polypeptides depending on the starting material. In table 1, the mass spectra, in table 2, the retention times, and in FIGS. 1 and 2 the SDS page gel electrophoresis diagrams corresponding to the different growth factors of the invention are listed.

TABLE 1

| Growth Factor Complex: Mass Spectra (Molecular Weights in Dalton) | | | | | | |
|---|---|---|---|---|---|---|
| GFC from cow's milk dialyzed | GFC from human milk, dialyzed | GFC from mare's milk, dialyzed | GFC from human blood, dialyzed | GFC from whey, dialyzed | GFC from hen's eggs, dialyzed | GFC from fish roe, dialyzed |
| | | | | | | 1,744.0 |
| | | | | | | 1,901.0 |
| | | | | | | 2,117.0 |
| | | | | | | 2,263.0 |

TABLE 1-continued

Growth Factor Complex: Mass Spectra (Molecular Weights in Dalton)

| GFC from cow's milk dialyzed | GFC from human milk, dialyzed | GFC from mare's milk, dialyzed | GFC from human blood, dialyzed | GFC from whey, dialyzed | GFC from hen's eggs, dialyzed | GFC from fish roe, dialyzed |
|---|---|---|---|---|---|---|
| | | | | | | 2,345.0 |
| | | | | | | 2,424.0 |
| | | | | | | 2,516.0 |
| 3,995.5 | | | | | | 4,845.0 |
| | | | 5,080.0 | | | |
| | | | 5,929.0 | | | |
| 7,132.5 | 7,500.0 | 7,121.1 | 7,412.0 | | | |
| | | | 7,945.0 | | | |
| | | | 8,481.1 | | | |
| 9,248.6 | | | | 9,201.2 | 9,762.5 | |
| | 11,102.8 | | 11,703.0 | | | |
| 14,186.0 | 14,142.2 | 14,217.1 | 14,489.0 | 14,192.4 | | |
| | | 14,620.2 | 14,647.0 | | | |
| | | | 15,887.0 | | | |
| 18,287.0 | | | | 18,367.4 | 17,086.6 | |
| 18,372.0 | 18,461.6 | | | | 19,441.4 | |
| | | 24,885.3 | | | | |
| | | 25,810.2 | | 25,281.1 | | |
| 28,331.5 | 28,283.0 | 28,660.0 | 27,783.0 | | | |
| | | | 30,391.0 | | | |
| 32,480.3 | | | | 32,573.6 | 33,971.1 | |
| | | | | 36,644.3 | | |

TABLE 2

Growth Factor Complex: HPLC Retention Times (in min)

Column: Nucleosil $C_{18}$
Wavelength of detection: 275 nm
Mobile phase: gradient with citric acid 0.1 M and acetonitrile
Samples: dissolved in 0.1 M citric acid (1% solution)

| GFC from cow's milk powder | GFC from cow's milk whey | GFC from human milk | GFC from hen's eggs | GCF from fish roe | Water for dialysis |
|---|---|---|---|---|---|
| 0.86 | | 0.87 | 0.84 | 0.85 | |
| 1.21 | 1.23 | 1.17 | 1.38 | 1.24 | 1.21 |
| 1.74 | 1.71 | 1.72 | 1.79 | 1.78 | 1.77 |
| | | | | | 1.94 |
| 2.44 | 2.38 | 2.63 | | 2.63 | 2.62 |
| 2.88 | | 2.93 | 2.86 | 2.91 | |
| 3.89 | 3.47 | 3.86 | 3.85 | 3.93 | 3.91 |
| | | | | | 4.67 |
| | | 5.03 | | 5.04 | |
| 6.99 | 6.45 | | | 6.93 | |
| | | | | 7.36 | |
| | | 7.75 | | | |
| | | | | 8.54 | |
| | | 8.71 | | | 8.82 |
| | 9.17 | 9.28 | | | |
| 9.49 | 9.62 | | 9.55 | 9.31 | |
| | | | | 9.79 | |
| | | | | 9.82 | |
| 10.26 | | 10.02 | | | 10.10 |
| | | 10.53 | 10.45 | | |
| | 12.02 | 11.79 | | | |
| | | | 13.07 | 12.93 | |
| | | 13.32 | 13.20 | | |
| | | | | 14.32 | |
| | | | | 15.06 | |
| | | 16.39 | | | 16.46 |
| 17.84 | | 17.83 | | | |
| 18.42 | | 18.50 | | 18.35 | 18.59 |
| 19.02 | | | | | |

The Growth Factor Complex according to the invention consists predominantly of lactose and contains about 2% to 15% of proteins. The protein portion may be strongly increased by dialysis. The protein content is determined according to the method of M. M. Bradford, Analytical Biochemistry, 1976, 72, 248–254:

| | |
|---|---|
| GFC from cow's milk powder: | 5.0% per weight of proteins |
| GFC from cow's milk powder, dialyzed: | 21.0% per weight of proteins |
| GFC from cow's milk whey: | 5.0% per weight of proteins |
| GFC from human milk: | 14.5% per weight of proteins |
| GFC from human milk, dialyzed: | 76.0% per weight of proteins |
| GFC from hen's eggs: | 10.5% per weight of proteins |
| GFC from fish roe: | 2.5% per weight of proteins |

After appropriate formulation with physiologically well tolerated auxiliaries and carrier materials, the Growth Factor Complex according to the invention has many possible medical and cosmetic applications, e.g.:
- for the treatment of wounds, burns, hematomas, eczemas, ulcers asf. with accelerated healing,
- for the treatment of the mucous membrane of the mouth, such as e.g. parodontosis, after tooth extractions asf. with accelerated healing,
- for the treatment of the mucous membrane of the nose, such as e.g. dry mucous membrane of the nose, tendency of bleeding, after operations asf. with accelerated healing,
- for the improvement of the dermis structure, such as e.g. improved scarring, cellulitis, senile skin asf.,
- for the treatment and prophylaxis of alopecia,
- for the treatment of cancer, such as e.g. skin cancer, lung cancer, stomach cancer asf.,
- for the treatment of gastrointestinal disturbances, illnesses and ulcers,
- for the treatment and prophylaxis of osteoporosis,
- as food supplement, e.g. for infant nutrition, parenteral nutrition asf., for the development of muscular mass, and in veterinary medicine for the increase of milk production in mammals.

The Growth Factor Complex of the invention may be processed as active ingredient into all customary galenic forms used for the indications mentioned. The content of the active ingredient (Growth Factor Complex) in compositions may be 0.001% to 99%, preferably 0.01% to 50% and particularly preferable 0.1% to 10%. Quite particularly preferred is a content of 0.5% for topical use and of 75% for oral use.

The Growth Factor Complex may be processed into all compositions that are used for local treatment. Such compositions are e.g. topical applications for skin and mucous membranes such as ointments, creams, gels, pastes as well as also tooth pastes, emulsions, solutions, mouthwashes, sprays or as bath additives, plasters and gauzes containing ointment or paste.

The Growth Factor Complex can also be processed into parenteral medical preparations e.g. as solutions for infusions and injections.

Oral compositions are e.g. tablets and sugar-coated tablets which disintegrate in the stomach fluid, or other solid preparations, so-called osmotic pump systems, mono- and polylayered solid preparations which ensure a delayed liberation of the Growth Factor Complex, pellets in capsules or compressed pellets for either immediate or delayed liberation of the Growth Factor Complex, solutions in soft gelatine capsules or hard gelatine capsules sealed by use of specific methods, preparations soluble in water or other beverages such as effervescent tablets, effervescent granulates, solution tablets or solution granulates, liquid preparations such as drops or syrups for consumption as concentrate or diluted in water and other beverages.

The invention further includes a process for the manufacture of these medicaments and cosmetics, which is characterized in that a therapeutically active amount of the Growth Factor Complex together with a physiologically inert excipient is brought into a galenic form of administration.

For the manufacture of pharmaceutical preparations, conventional methods as dissolving, lyophilization, mixing and suspending processes are used.

For the manufacture of topical compositions, aqueous solutions of the Growth Factor Complex are suitable. These are processed into a hydrophilic ointment base e.g. macrogol or polyethylene glykol ointment, to creams containing hydrophobic lipid constituents, water and tensides, to gels with hydrophilic macromelucular compounds such as gelatine and cellulose ether, to pastes from a highly concentrated suspension ointment and to emulsions using oil, gum arabic and water. The production of the topical compositions is performed with conventional methods.

For parenteral administration aqueous solutions are most suitable, but also suspensions of the active ingredient such as oily suspensions for injection; suitable lipophil solvents or vehicles are plant oils e.g. sesame oil, fatty acid esters e.g. ethyl oleate and triglycerides; or aqueous suspensions for injection which contain compounds that increase the viscosity e.g. sodium carboxymethylcellulose, sorbitol and/or dextran and, if desired, stabilizing agents. Compositions for oral use may be obtained by combining the Growth Factor Complex with solid carrier materials, the resulting mixture is, if desired, granulated and the mixture or granulate, if desired or necessary, is processed into tablets or dragee cores after the addition of suitable auxiliary compounds. Suitable carrier materials are preferably filling compounds such as sugars e.g. lactose, saccharose, mannitol or sorbitol and cellulose preparations and/or calcium phosphates e.g. tricalcium phosphate or calcium hydrogen phosphate; also suitable are binding agents such as starch paste from e.g. corn, wheat, rice or potatoes, or gelatine, tragacanh gum, methyl cellulose, hydroxy propylmethyl cellulose, sodium carboxymethyl cellulose and/or polyvinyl pyrrolidone, and/or, if desired, blasting agents such as the above-mentioned starch forms; moreover carboxymethyl starch, crossmeshed polyvinyl pyrrolidone, agar, alginic acid or a salt thereof such as sodium alginate. Auxiliary agents are preferably flow regulating and lubricating agents e.g. silicic acid, talcum, stearic acid or salts thereof such as magnesium or calcium stearate and/or polyethylene glycol.

Dragee cores are provided with suitable coatings optionally resistant to gastric juice, using concentrated sugar solutions which optionally contain gum arabic, talcum, polyvinyl pyrrolidone, polyethylene glykol and/or titanic dioxide, varnish solutions in suitable organic solvents or solvent mixtures or, for the manufacture of coatings resistant to gastric juice, solutions of suitable cellulose preparations such as acetylcellulose phthalate or hydroxy propylmethyl cellulose phthalate.

Further useful compositions for oral application are two-piece hard gelatine capsules as well as soft closed gelatine capsules containing a tenderizer such as glycerin or sorbitol. The hard capsules may contain the Growth Factor Complex in granulate form e.g. by adding filling compounds such as lactose, binding agents such as starch and/or lubricating agents such as talcum or magnesium stearate, and optionally stabilizing agents. In soft capsules, the Growth Factor Complex is preferably dissolved or suspended in suitable liquids such as fatty oils, paraffin oil or liquid polyethylene glykols; stabilizing agents may also be added.

The present invention is illustrated by the following examples:

EXAMPLE 1

Extraction of Cows Dried Milk-GFC

| cow's dried milk, skimmed | 150 g |
|---|---|
| water, deionized | 700 g |
| lactic acid (80%) | 120 g |
| acetone | 3,560 g |
| water, deionized | 300 g |
| acetone | 150 g |

1. 150 g skimmed dried milk are slowly (within 5 min) added with stirring (Heidolph stirrer, about 200 rpm) to a beaker containing 700 g deionized water. The suspension is stirred for further 20 min.
2. 120 g of lactic acid are slowly (within 5 min) added and the suspension is stirred for further 15 min.
3. The content of the beaker is transferred to centrifuging vessels and centrifuged for 20 min at 6,000 rpm.
4. The supernatant aqueous solution is poured off. The solid pellet in the vessels is processed into a paste by adding about 300 g of deionized water and centrifuged again.
5. The supernatant aqueous solutions are combined and filtered through a liquor filter. The growth factors containing aqueous solution is light yellow and opalescent.
6. 3,560 g of acetone are slowly (within 5 min) added with stirring (Heidolph stirrer, 200 rpm) to 900 g of aqueous solution in an Erlenmeyer flask and the suspension is stirred for further 5 min. The resulting precipitate is allowed to settle over-night at room temperature.

7. The following day the precipitate is sucked off on a glass sinter suction filter G4, washed three times with 50 g of acetone and dried at 40° C. in a vacuum drying chamber, preferably under nitrogen gas.

Yield: about 58 g of cow's dried milk-GFC.

EXAMPLE 2
Extraction of Mother's Milk-GFC

| | |
|---|---|
| human milk | 600 ml |
| lactic acid (80%) | 90 ml |
| acetone | 1,500 ml |

1. 600 ml of human milk are centrifuged for 20 min at 6,000 rpm. The upper fatty layer is removed and the remaining solution is evaporated to 300 ml under vacuum.
2. 90 ml of lactic acid are added slowly (within 5 min) and the solution is stirred for further 15 min. The procedure of example 1, items 3 to 7, is followed.

Yield: about 40 g of mother's milk-GFC.

EXAMPLE 3
Extraction of Hen's Egg-GFC

| | |
|---|---|
| egg yolk | 6 |
| water, deionized | 200 ml |
| lactic acid (80%) | 100 ml |
| acetone | 1,500 ml |

1. 6 egg yolks are evaporated to dryness under vacuum (about 44 g of dry substance) and suspended in 200 ml of deionized water.
2. 100 ml of lactic acid are added slowly (within 5 min) to the suspension. A very fine, non filterable prepicipate is formed.
3. The suspension is dialyzed in a dialysis tube (cutoff: 3,000 MW) against water for two days.
4. 300 ml of the aquous solution from the dialysis tube are precipitated in an Erlenmeyer flask by adding 1,500 ml of acetone (slow addition, i.e. within 5 min) with stirring (Heidolph stirrer, 200 rpm). The mixture is stirred for further 5 min. The precipitate is allowed to settle over-night at room temperature.
5. The precipitate is sucked off the next day on a glass sinter suction filter G4, washed three times with 50 ml of acetone and dried at 40° C. in a vacuum drying chamber.

Yield: about 4 g of Hen's Egg-GFC.

EXAMPLE 4
Extraction of Fish Roe-GFC

| | |
|---|---|
| trout eggs | 100 g |
| water, deionized | 500 ml |
| lactic acid (80%) | 80 ml |
| acetone | 2,500 ml |

1. 100 g of trout eggs are disintegrated in 500 ml of deionized water using a mixer.
2. 80 ml of lactic acid are added slowly (within 5 min) and the suspension is stirred for further 15 min.
3. The resulting precipitate is transferred to centrifuging vessels and centrifuged for 20 min at 6,000 rpm. The supernatant growth factors containing aqueous solution (about 500 ml) is poured off.
4. 500 ml of the aqueous solution are precipitated in an Erlenmeyer flask by adding of 2,500 ml of acetone (slow addition, i.e. within 5 min) with stirring (Heidolph stirrer, 200 rpm). The mixture is stirred for further 5 min. The precipitate is allowed settle over-night at room temperature.
5. The precipitate is sucked off the next day on a glass sinter suction filter G4, washed three times with 50 ml of acetone and dried at 40° C. in a vacuum drying chamber.

Yield: about 1.5 g of fish roe-GFC.

EXAMPLE 5
Extraction of Human Blood-GFC

| | |
|---|---|
| human blood | 150 ml |
| water, deionized | 225 ml |
| lactic acid (80%) | 45 ml |
| acetone | 1,600 ml |

1. 150 ml of human blood are diluted with 225 ml of deionized water.
2. 45 ml of lactic acid are added slowly (within 5 min.) with stirring (Heidolph stirrer, about 200 rpm) and the suspension is stirred for further 15 min.
3. The resulting precipitate is transferred to centrifuge vessels and centrifuged for 20 min at 6,000 rpm. The supernatant growth factors containing aqueous solution (about 320 ml) is poured off.
4. 320 ml of the aqueous solution are precipitated in an Erlenmeyer flask by adding 1,600 ml of acetone (slow addition, i.e. within 5 min) with stirring (Heidolph stirrer, 200 rpm). The mixture is stirred for further 5 min. The precipitate is allowed to settle over-night at room temperature.
5. The precipitate is sucked off the next day on a glass sinter suction filter G4, washed three times with 50 ml of acetone and dried at 40° C. in a vacuum drying chamber.

Yield: about 22 g of human blood-GFC.

EXAMPLE 6
Extraction of Cow's Milk Whey-GFC

| | |
|---|---|
| dried whey from cow's milk | 100 g |
| water, deionized | 500 ml |
| lactic acid | 100 ml |
| acetone | about 3,500 ml |

1. 100 g of dried whey are disintegrated in 500 ml of deionized water with stirring (Heidolph stirrer, about 200 rpm).
2. 100 ml of lactic acid are added and the suspension is stirred for about 1 hour.
3. The resulting precipitate is transferred to centrifuge vessels and centrifuged for 20 min at 5,500 rpm. The supernatant growth factors containing aqueous solution (about 570 ml) is poured off.

4. The aqueous solution is divided into two parts and precipitated with stirring (Heidolph stirrer, 200 rpm) by adding each 1,500 ml of acetone. The precipitate is allowed to settle over-night at room temperature.
5. The precipitate is sucked off the next day on a glass sinter suction filter G4, washed three times with 50 ml of acetone and dried at 40° C. in a vacuum drying chamber.

Yield: about 73.4 g of cow's milk whey-GFC.

EXAMPLE 7
GFC-wound Gel 0.5%

| 100 g of wound gel contain: | |
|---|---|
| carbopol 980 NF | 0.50 g |
| water, deionized | 92.84 g |
| tris(hydroxymethyl)-aminomethane 1 M in H$_2$O | 6.16 g |
| Growth Factor Complex (GFC) | 0.50 g |

60 g of deionized water are stirred in a 200 9 beaker at medium speed. 0.5 g of carbopol 980 NF are added slowly with stirring, stirred for further 10 min and allowed to swell for 15 min. 5 g of tris(hydroxymethyl)-aminomethane are weighed into a test tube, 0.5 g of GFC are added and suspended well. The GFC solution is added to the gel mass and mixed with a spatula. The pH value is adjusted to 6–7 with 1 M tris(hydroxymethyl)-aminomethane with stirring. With further stirring, the gel mass is diluted to 100 g with deionized water and stirred for about further 5 min.

EXAMPLE 8
GFC-tooth Paste 0.5%

| 100 g of tooth paste contain: | |
|---|---|
| Growth Factor Complex (GFC) | 0.50 g |
| calcium carbonate | 37.00 g |
| aerosil 200 | 1.00 g |
| glycerine | 25.00 g |
| paraffin | 0.50 g |
| peppermint oil | 1.00 g |
| Na-fluoride | 0.76 g |
| saccharine | 0.01 g |
| water, deionized | 27.28 g |
| carboxymethylcellulose | 0.80 g |
| Na-lauryl sulfate | 2.00 g |
| water, deionized | 4.15 g |

GFC, calcium carbonate and aerosil 200 are micronized with a pestle in a mortar. Glycerine, paraffin and peppermint oil are added and pasted with the pestle. Deionized water, Na-fluoride and saccharine are stirred for 5 min in a beaker and added to the pasted calcium carbonate mixture. Na-lauryl sulfate is added to a beaker and the remaining water is added. After heating to about 30° C. and suspending with stirring, the resulting suspension is added to the pasted calcium carbonate mixture. The paste is stirred well by hand and passed through a 3-roller-mill at grade 3; the mass is stirred again. The pH value of the resulting paste is 10. If desired for organoleptic reasons, the pH value may be adjusted to a neutral or slightly acidic value with citric acid.

EXAMPLE 9
GFC-solution 2% for Injection

| Composition for 1 liter solution for injection: | |
|---|---|
| Growth Factor Complex | 20.0 9 |
| ascorbic acid | 45.0 g |
| water for injection | 935.0 g |

935 g of water for injection are weighed into an Erlenmeyer flask. 45 g of ascorbic acid are added and (with the flask closed) dissolved within about 10 min of stirring at 900 rpm. 20 g of GFC are added and the solution is stirred for about 1 hour until the GFC has almost dissolved. The solution is filtered through a sterile filter directly into a sterile brown glass bottle.

EXAMPLE 10
GFC-powder for Injection 100 mg

| Composition for 200 bottles containing each 100 mg of GFC: | |
|---|---|
| Growth Factor Complex | 20.0 g |
| Composition for 200 solvent ampules containing each 5 ml: | |
| ascorbic acid | 45.0 g |
| water for injection | 935.0 g |

100 mg of GFC are weighed into sterile flasks. 935 g of water for injection are weighed into an Erlenmeyer flask. 45 g of ascorbic acid are added to the water and (with the flask closed) dissolved within about 10 min of stirring at 900 rpm. The solution is filtered through a sterile filter directly into a sterile brown glass flask. 5 ml of the solution are transferred to each solvent ampule. Before use, the content of a solvent ampule is injected into a sterile, GFC-containing flask with an injection needle, and the GFC is dissolved by carefully shaking the flask.

EXAMPLE 11
GFC-tablets 500 mg

| 1000 tablets contain: | |
|---|---|
| Growth Factor Complex | 500.0 g |
| cellulose, microcrystalline | 86.0 g |
| Na-carboxymethyl starch | 50.6 g |
| povidone K30 | 30.0 g |
| silicic acid, micronized, porous, synthetic | 3.2 g |
| ricinus oil, hardened | 5.2 g |
| isopropanol | for moistening |

GFC, cellulose, Na-carboxymethyl-starch and providone are weighed, sieved (mesh width 710 µm) and mixed. The mixture is micronized in a mortar with a pestle and moistened with about 180 g of isopropanol. The moist mixture is dried for 3 hours at 50° C. in a drying chamber and sieved (mesh width 710 µm). Silicic acid and ricinus oil are added to the granulate and the mixture is mixed well in a closed container. Tablets are pressed on a tablet press (Korsch EKO) with a stamp of 13 mm diameter, yielding tablets with a weight of 675 mg (corresponding to 500 mg of GFC).

We claim:

1. A process for the extraction of a Growth Factor Complex from a starting material containing natural growth factor, which comprises the following steps:
   a) water is added to the starting material;
   b) the pH value is adjusted to 2.5 to 3.2 by the addition of acid, resulting in a first precipitate;

c) the resulting first precipitate is separated from supernatant;

d) an organic solvent miscible with water is added to the supernatant in step c), resulting in a second precipitate;

e) the resulting second precipitate is separated and dried and contains the extracted growth factor complex.

2. The process according to claim 1, wherein the natural growth factor containing materials are selected from the group consisting of milk from mammals, whey, bird's eggs, fish roe, blood from mammals, urine from mammals, bee's honey and plant seeds.

3. The process according to claim 1, wherein a material selected from the group consisting of non-oxidizing mineral acid; a mono-, di- or tricarboxylic acid; and a hydroxy carboxylic acid derived from mono-, di or tricarboxylic acid is used for adjusting the pH value from 2.5 to 3.2.

4. The process according to claim 1, wherein a lower alkanol or a lower dialkyl ketone is used as the organic solvent miscible with water for separating the Growth Factor Complex.

5. The process according to claim 1, wherein the organic solvent miscible with water and the growth factors containing aqueous solution are mixed at a volume ratio of 2:1 to 10:1.

6. The process according to claim 1, wherein the Growth Factor Complex obtained after drying is extracted with a fat soluble solvent.

* * * * *